United States Patent
Hiramoto et al.

(10) Patent No.: US 6,316,776 B1
(45) Date of Patent: Nov. 13, 2001

(54) CHARGED PARTICLE BEAM APPARATUS AND METHOD FOR OPERATING THE SAME

(75) Inventors: Kazuo Hiramoto; Hiroshi Akiyama, both of Hitachioota; Koji Matsuda; Tetsuro Norimine, both of Hitachi; Masahiro Tadokoro, Hitachioota, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/388,437

(22) Filed: Sep. 2, 1999

Related U.S. Application Data

(63) Continuation of application No. 08/916,332, filed on Aug. 22, 1997, now Pat. No. 5,969,367.

(30) Foreign Application Priority Data

Aug. 30, 1996 (JP) .................................................. 8-229699

(51) Int. Cl.[7] .................................................. H05H 9/00
(52) U.S. Cl. .................. 250/492.3; 315/501; 315/507
(58) Field of Search ........................... 250/492.3, 505.1, 250/398; 315/501, 505, 507

(56) References Cited

U.S. PATENT DOCUMENTS

| | | |
|---|---|---|
| 5,006,759 | 4/1991 | Krispel . |
| 5,019,713 | 5/1991 | Schmidt . |
| 5,260,581 | 11/1993 | Lesyna et al. . |
| 5,382,914 | 1/1995 | Hamm et al. . |
| 5,585,642 | 12/1996 | Britton et al. . |
| 5,744,919 | 4/1998 | Mishin et al. . |
| 5,969,367 | * 10/1999 | Hiramoto et al. ............... 250/492.3 |

FOREIGN PATENT DOCUMENTS

| | | |
|---|---|---|
| 44 11 171 A1 | 10/1995 | (DE) . |
| 5-198397 | 8/1993 | (JP) . |

OTHER PUBLICATIONS

Th. Haberer et al., "Magnetic Scanning System for Heavy Ion Therapy", Nuclear Instrument Methods in Physical Research, Jun. 10, 1993, vol. A330, Nos. 1,2, pp. 296–305.

* cited by examiner

Primary Examiner—Kiet T. Nguyen
(74) Attorney, Agent, or Firm—Antonelli, Terry, Stout & Kraus, LLP

(57) ABSTRACT

A method of irradiation with a charged particle beam and an irradiation apparatus wherein the charged particle beam supplied from an accelerator and extracted from the irradiation apparatus. The irradiation apparatus includes an electromagnet for scanning with the charged particle beam. The method includes the steps of stopping the extraction of the charged particle beam from the irradiation apparatus, changing an irradiation point of the charged particle beam by controlling the electromagnet under a condition when the extraction is stopped, and resuming the extraction of the charged particle beam from the irradiation apparatus after changing the irradiation point.

7 Claims, 15 Drawing Sheets

AFFECTED PART

CHARGED PARTICLE BEAM APPARATUS AND METHOD FOR OPERATING THE SAME

CROSS REFERENCE TO RELATED APPLICATION

This is a continuation of U.S. application Ser. No. 08/916,332, filed Aug. 22, 1997, now U.S. Pat. No. 5,964,367, the subject matter of which is incorporated by reference herein.

BACKGROUND OF THE INVENTION

A charged particle beam apparatus, which is disclosed in JP-A-5-40479 (1993), will be explained with reference to FIG. 1.

In FIG. 1, the charged particle beam 82 is directed along a path extending in the direction Z. When sine wave currents, having a phase difference of 90° with respect to each other, are supplied to a scanning electromagnet 80 to produce a magnetic field in the X direction and to a scanning electromagnet 81 to produce a magnetic field in the Y direction, respectively, the charged particle beam is scanned circularly by the magnetic fields generated by the respective electromagnets. When the circularly scanned charged particle beam is projected onto a scatterer 83, the size of the charged particle beam is broadened, and the dose in the irradiation region is distributed as shown in FIG. 2. The dose becomes uniform in the region within a range of 2r, but the dose in the region outside the range 2r decreases more for positions farther from the central position and becomes uneven. Accordingly, the uneven irradiation region was cut by a collimator, and only the irradiation region having a uniform dose was used for irradiating an affected portion.

The patent JP-A-7-275381 discloses a method, by which electromagnets are controlled so that the irradiation region is formed in an arbitrary shape.

SUMMARY OF THE INVENTION

However, in accordance with the prior art, the loss of a part of the charged particle beam is significant, because the uneven irradiation region eliminated by the collimator. Furthermore, in order to obtain a large irradiation geld, the thickness of the scatterer 38 for increasing the size of the beam must be increased, causing a further increase in the loss of charged particle beam energy.

One of the objects of the present invention is to provide a charged particle beam apparatus, wherein the loss of energy in the charged particle beam is decreased, and to a method for operating the same.

The present invention relates to a charged particle beam apparatus of the type used for cancer therapy, diagnosis of affected parts, and other applications.

The feature of the present invention to achieve the above objects is in the steps of broadening the size of the charged particle beam using a scatterer, switching the extraction of and stopping the charged particle beam by an extraction switching means, setting an irradiation position of the charged particle beam using an electromagnet, and changing the irradiation position or the irradiation range by controlling the electromagnet with a controlling apparatus during the stopping of the charged particle beam.

In accordance with the above feature, the uneven irradiation region around an irradiation target can be minimized and the loss of the charged particle beam can be reduced in comparison with a case wherein the charged particle beam is enlarged by the scatterer so as to cover all of the region of the irradiation target, because the controlling apparatus changes the irradiation position or the irradiation range during the time the extraction of the charged particle beam is stopped by the extraction switching means, and then, the irradiation target of the charged particle beam is irradiated per each of the irradiation positions or the irradiation range.

Furthermore, in comparison with a case when where scatterer is not used, the irradiation position is changed only a small number of times, and the control is simple, because the size of the charged particle beam is large.

Another feature of the present invention involves charging the irradiation position on the basis of the size of the enlarged charged particle beam by the controlling apparatus. An even irradiation region having a uniform irradiation dose can be formed by overlapping the charged particle beams, and the irradiation target can be irradiated uniformly with the charged particle beam, because the irradiation close of the charged particle beam, which is enlarged by the scatterer, distributes diametrically in approximately a Gaussian distribution with a center at the irradiation position.

Another feature of the present invention involves the steps of determining a target of the irradiation dose in the irradiation region of the irradiation target by an apparatus for setting the target of the irradiation dose, determining the irradiation dose of the charged particle beam in the respective irradiation regions by an irradiation does measuring apparatus, and switching the extraction and stopping the charged particle beam by an extraction switching means on the basis of the target of the irradiation dose and the observed irradiation dose determined by the irradiation does measuring apparatus.

In accordance with the above feature, the target of the irradiation can be irradiated with an uniform beam density even if the intensity of the beam varies depending on time, because the irradiation can be continued by the extraction switching means until the irradiation dose at the irradiation region reaches the target of the irradiation dose.

When the extraction switching means is a radio frequency supplying apparatus for supplying radio frequency electromagnetic field including frequencies of bettor oscillation of the charged particle beam, which circulates in the charged particle accelerator, to the charged particle beam, the amplitude of the bettor oscillation of the charged particle beam is increased by supplied radio frequency electromagnetic field when the bettor oscillation of the charged particle beam circulating the charged particle accelerator is in a resonance condition, and the charged particle beam is extracted from the charged particle accelerator by exceeding a stability limit of the resonance. At this time, since the charged particle beam is extracted with a constant rate, the irradiation target is irradiated with the charged particle beam with an uniform beam density.

Another feature of the present invention is in changing the energy of the charged particle beam by energy varying means, and the irradiation range of the irradiation target can be changed by varying the energy of the charged particle beam during stopping the irradiation.

Another feature of the present invention is in that the charged particle accelerator is provided with an extraction switching means for switching the extraction and stopping the charged particle beam, a charged particle beam transport system is provided with a transportation switching apparatus for switching the transportation and stopping the charged particle beam, and the irradiation apparatus comprises a scattered for enlarging the charged particle beam, an electromagnet for setting the irradiation position of the charged particle beam, and a controlling apparatus for varying the irradiation position based on the size of the enlarged charged particle beam.

In accordance with the above feature, the charged particle beam is irradiated to the irradiation target with the irradiation apparatus by extracting the charged particle beam which is circulating the charged particle accelerator to the irradiation apparatus by the extracting switching means, and transporting the charged particle beam to the irradiation apparatus by the transportation switching apparatus. The irradiation of the charged particle beam to the irradiation target is slopped by slopping the extraction of the charged particle beam from the charged particle accelerator to the irradiation apparatus by the extraction switching means, or stopping the transportation of the charged particle beam by the transportation switching apparatus. Desirable safety can be ensured, because the switching of the irradiation can be performed by two switching means different from each other. When the extraction switching means, or the transportation switching apparatus terminates the extraction of the beam, the controlling apparatus varies the irradiation position to the next point based on the size of the charged particle beam which is enlarged by the scatterer, and the irradiation is performed with an equal dose at every irradiation positions, the charged particle beam is pertly overlapped to form an irradiation region of an uniform irradiation dose, and the irradiation target can be irradiated with the charged particle beam uniformly, because the irradiation dose of the charged particle beam which is enlarged by the scatterer has a Gaussian distribution in the radial direction with a center at the irradiation position.

Furthermore, since the uneven irradiation region formed surrounding the uniform irradiation region can be reduced, the loss of the charged particle beam can be decreased. In comparison with a case when the scatterer is not used, the number of changing the irradiation position can be reduced, because the size of the beam is larger then the ease no scatterer is used, and controlling can be simplified.

Another feature of the present invention is in being provided with a movement detecting means for detecting the movement of patient, and controlling the extraction switching means based on the movement of the patient detected by the movement detecting means by the controlling apparatus.

In accordance with the above feature, the irradiation target can be irradiated precisely, because the irradiation of the charged particle beam is performed when the patient is almost still by defecting the movement of body of the patient caused by breathing and coughing with the movement detecting means.

In a case of cancer therapy by the charged particle beam, the energy of the charged particle beam must be changed depending on the depth of the irradiation target. In this case, the energy of the charged particle beam circulating in the charged particle accelerator is changed in an accelerating step, or the energy of the extracted charged particle beam is changed by placing a plate-shaped material such as graphite at a path of the charged particle beam in the irradiation apparatus.

Another feature of the present invention is in the steps of broadening the size of the charged particle beam by a scatterer, extracting the charged particle beam from a charged particle accelerator by an extraction means, setting an irradiation position or an irradiation range of the charged particle beam by an electromagnet, and changing the irradiation position or the irradiation range by controlling the electromagnet with a controlling apparatus during any one of operations of injection, acceleration, and deceleration of the charged particle accelerator.

In accordance with the above feature, the uneven irradiation region around an irradiation target can be minimized and the loss of the charged particle beam can be reduced in comparison with a case, wherein the charged particle beam is enlarged by the scatterer so as to cover all the region of the irradiation target, because the controlling apparatus changes the irradiation position or the irradiation range during any one of operations of injection, acceleration, and deceleration of the charged particle accelerator after the extraction by the extraction means, and then, the irradiation target of the charged particle beam is irradiated per each of the irradiation positions or the irradiation range.

Furthermore, in comparison with a case when the scatterer is not used, the number of changing the irradiation position is small, and control is simple, because the size of the charged particle beam is large.

Another feature of the present invention is in the steps of broadening the size of the charged particle beam by a scatterer, moving the charged particle beam to an extracting orbit from a circulating orbit by a kicker electromagnet, setting an irradiation position or an irradiation range of the charged particle beam by an electromagnet, and changing the irradiation position or the irradiation range by controlling the electromagnet with a controlling apparatus during any one of operations of injection, acceleration, and deceleration of the charged particle accelerator.

In accordance with the above feature, the uneven irradiation region around an irradiation target can be minimized and the loss of the charged particle beam can be reduced in comparison with a case, wherein the charged particle beam is enlarged by the scatterer so as to cover all the region of the irradiation target, because the controlling apparatus changes the irradiation position or the irradiation range while the beam is not extracted during any one of operations of injection, acceleration, and deceleration of the charged particle accelerator after the extraction as the result that the kicker electromagnet moves the charged particle beam to an extraction orbit from a circulating orbit, and then, the irradiation target of the charged particle beam is irradiated per each of the irradiation positions or the irradiation range.

Furthermore, in comparison with a case when the scatterer is not used, the number of changing the irradiation position is small, and control is simple, because the size of the charged particle beam is large. Furthermore, an even irradiation region haying en uniform irradiation dose can be formed by overlapping the charged particle beams, and the irradiation target can be irradiated uniformly with the charged particle beam, because the irradiation close of the charged particle beam, which is enlarged by the scatterer, distributes diametrically in approximately a Gaussian distribution with a center at the irradiation position.

The beam is extracted as soon as the kicker electromagnet is excited, and the extraction can be completed almost while the beam circulates only one round in the accelerator because the time of being excited is one circulation time or so. Then, the charged particle beam, which is extracted in such a short time as about one circulation time of the beam, can be used continuously.

DETAILED DESCRIPTION OF THE PREFERRED EMBODIMENTS

Embodiment 1

Figure 3:
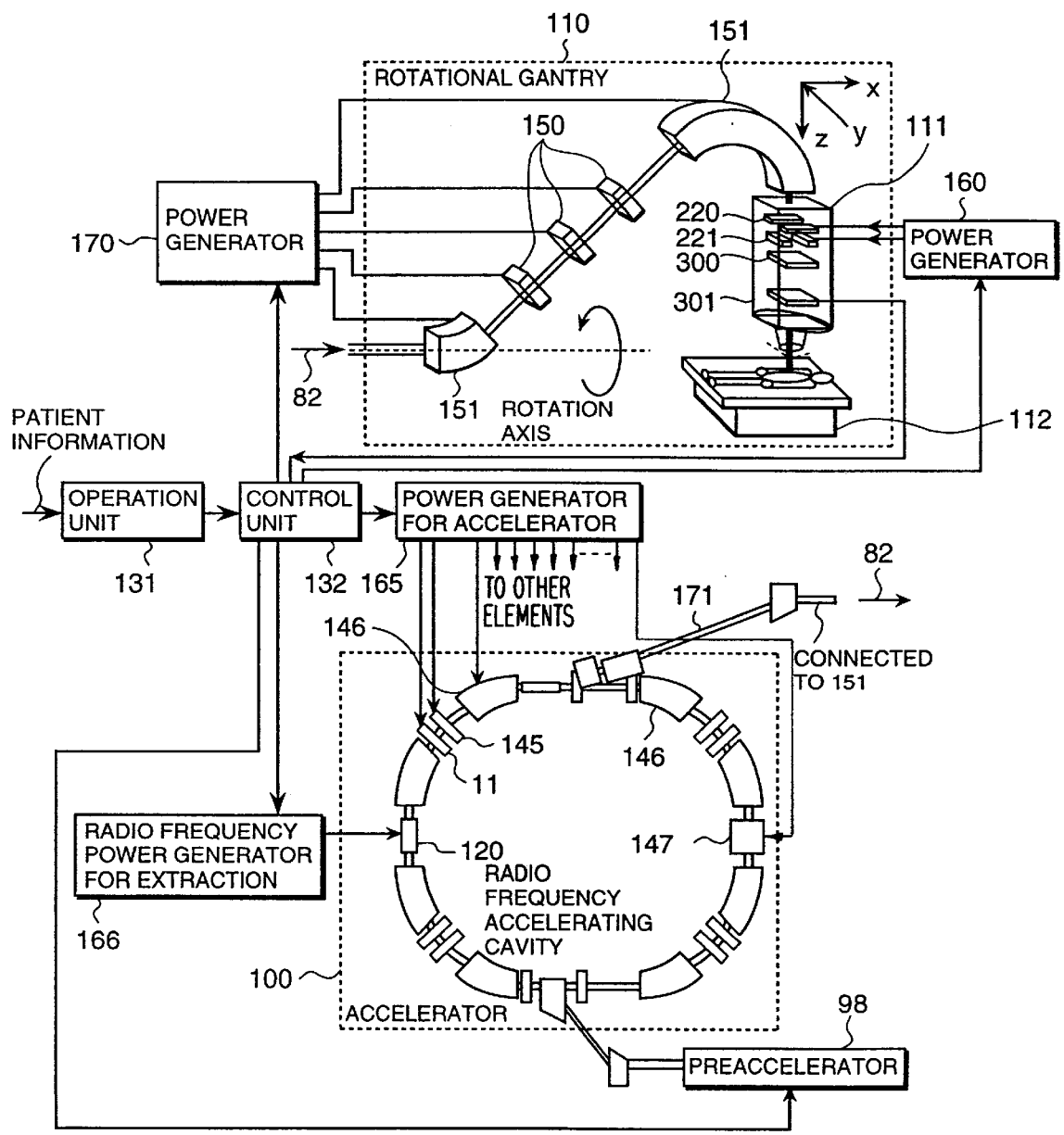
FIG. 3 is a schematic diagram showing a first embodiment of a charged particle beam apparatus of the present invention.

Referring now to FIG. 3, the first embodiment of a charged particle beam apparatus according to the present invention will be described hereinafter.

The charged particle beam apparatus of the present invention mainly includes a pre-accelerator 98, an accelerator of the synchrotron type 100, a rotational gantry 110, an operation unit 131 and a control unit 132.

Ions of low energy from the pre-accelerator 98 are injected into the accelerator 100 and they are accelerated by the accelerator 100 and then extracted to the rotational gantry 110 inside a treatment room so that an ion beam may be provided for use in medical treatment.

Main components constituting the accelerator 100 will be described. The accelerator 100 is an accelerator utilizing the diffusion resonance extraction method for beam extraction in which betatron oscillation of a charged particle beam circulating through the accelerator 100 is brought into a resonance state, and a radio frequency electromagnetic field is applied to the circulating charged particle beam to increase the betatron oscillation thereof to thereby ensure that a stability limit of resonance can be exceeded and the charged particle beam can be extracted from the accelerator.

The accelerator 100 includes bending electromagnets 146 for bending the circulating charged particle beam, a radio frequency accelerating cavity 147 for applying energy to the circulating charged particle beam, pairs of a quadrupole electromagnet 145 and a multipole electromagnet 11 for generating magnetic fields to cause the circulating charged particle beam to generate the stability limit of the resonance of the betatron oscillation, and a radio frequency applying unit for extraction 120, which applies a radio frequency to the circulating charged particle beam to increase the betatron oscillation. The accelerator 100 further includes a power generator for acceleration 165, which supplies current to the bending electromagnets 146, quadrupole electromagnets 145, and multipole electromagnets 11 and which supplies electric power to the radio frequency accelerating cavity 147, and a radio frequency generator for extraction 166, which supplies electric power to the radio frequency applying unit for extraction 120.

The patient is irradiated by the beam, which is extracted from the accelerator 100 and is transported to the treatment room by the transport system 171 via the rotational gantry 110.

The rotational gantry 110 will be described hereinafter. The rotational gantry 110 includes quadrupole electromagnets 150 and bending electromagnets 151 which are adapted to transport a beam extracted from the accelerator 100 to an irradiation target, and a power generator 170 for supplying current to the quadrupole electromagnets 150 and the bending electromagnets 151.

The rotational gantry 110 further includes an irradiation nozzle. The irradiation nozzle includes electromagnets 220 and 221 which are provided downstream of one of the bending electromagnets 151 and are operative to deflect the extracted beam in x and y directions, respectively. Here, the x direction is parallel to the bending plane of the one bending electromagnet 151 and the y direction is transverse to the bending plane of the one bending electromagnet 151. The electromagnets 220 and 221 are connected to a power generator 160 for supplying current to them. A scatterer 300 for enlarging the size of the beam is provided downstream of the electromagnets 220 and 221. An irradiation dose monitor 301, for determining the irradiation close distribution of the beam, is installed downstream of the scatterer 300. A collimator 225 is installed before the patient, who represents the irradiation target, in order to prevent the normal tissue around the affected part from irradiation damage.

Figure 4:
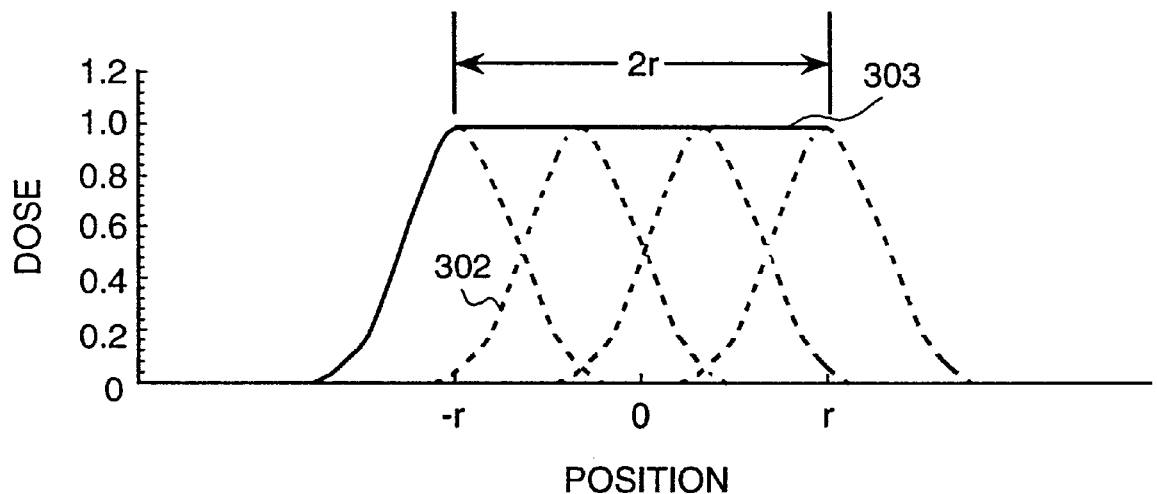
FIG. 4 is a graph indicating an intensity distribution of a beam enlarged by a scatterer.

The beam intensity distribution 302, which is enlarged by the scatterer 300, is indicated in FIG. 4, the beam enlarged by the scatterer has approximately a Gaussian distribution. Accordingly, if the irradiation position is shifted about a half of the beam size, which is enlarged by the scatterer 300, as shown in FIG. 4, during a time when the extraction of the beam from the accelerator is stopped, and an equivalent irradiation is resumed at each of the shifted positions, almost a similar irradiation dose 303 can be obtained at any places including the places other than the irradiation center position of the beam, by overlapping the irradiation. Therefore, an affected part can be irradiated uniformly by repeating the sequential steps of (1) confirming by the irradiation dose monitor 301 that the proper irradiation dose predetermined by the therapy plan is being irradiated, (2) stopping the extraction of the beam from the accelerator, (3) shifting the irradiation position, and (4) resuming the extraction of the beam.

Figure 1:
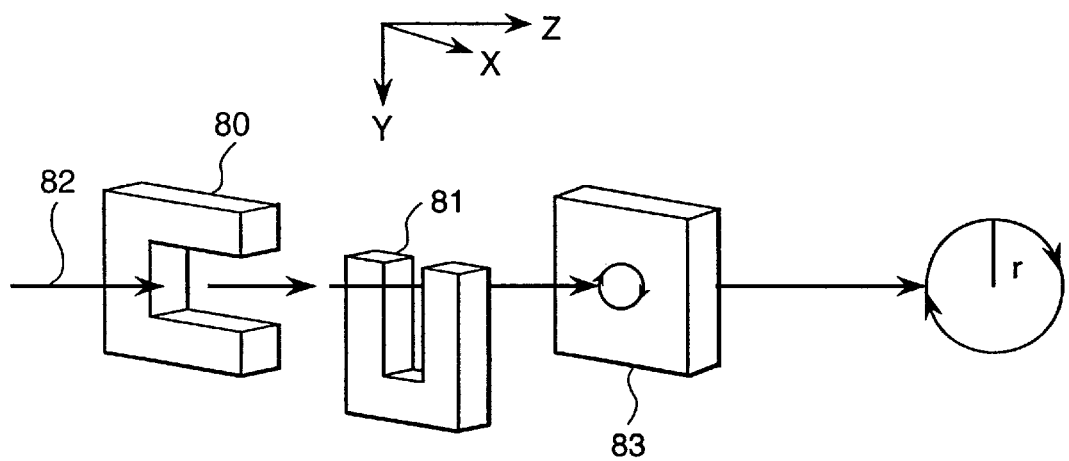
FIG. 1 is a schematic diagram showing elements of a conventional charged particle beam apparatus.
Figure 2:
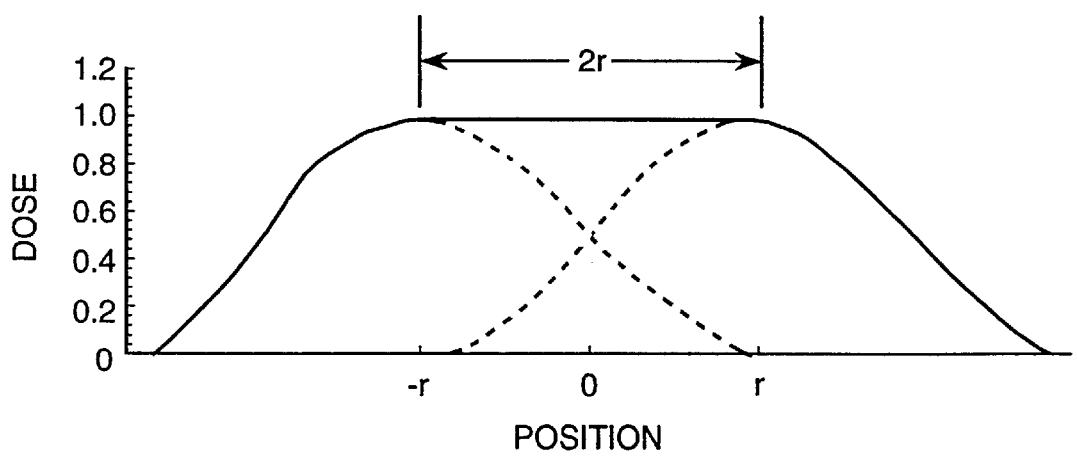
FIG. 2 is a graph indicating an intensity distribution of a beam enlarged by the conventional charged particle beam apparatus.

On the other hand, as can be seen in FIG. 4, the region outside the area defined by 2r from the center of the irradiation is irradiated unevenly. However, the area of the uneven region is smaller in comparison with a case when an irradiation region having a uniform irradiation dose is realized by circular scanning of the charged particle beam in the irradiation region 2r, as shown in FIG. 2.

Therefore, the loss of energy in the charged particle beam can be reduced. Furthermore, since the size of the beam enlarged by the scatterer 300 is smaller than the size of the beam when circular scanning of the charged particle beam is performed, the thickness of the scatterer 300 can be decreased. Therefore, the energy loss of the charged particle beam can be further reduced.

Figure 5:
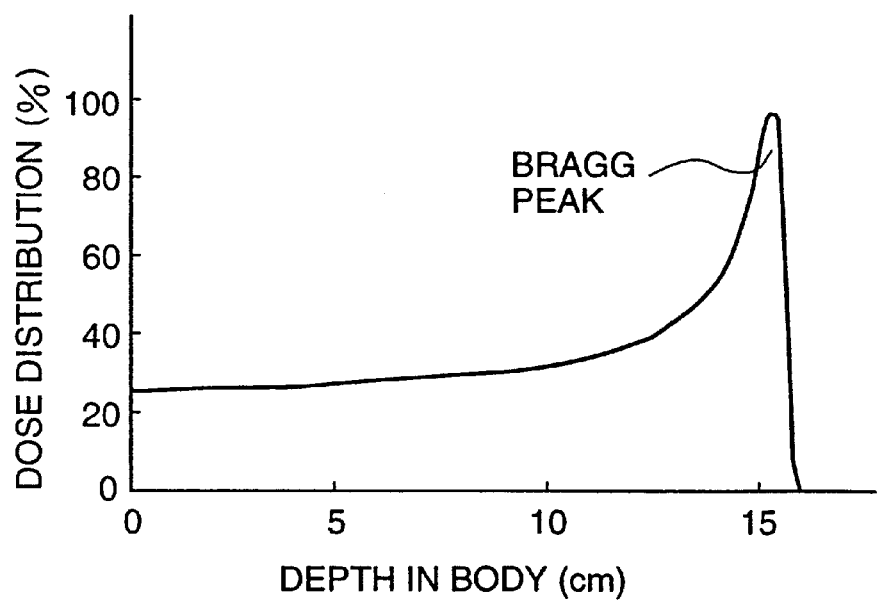
FIG. 5 is a graph indicating an example of the relationship between depth of a part to be treated and the irradiation dose of an ion beam.
Figure 6:
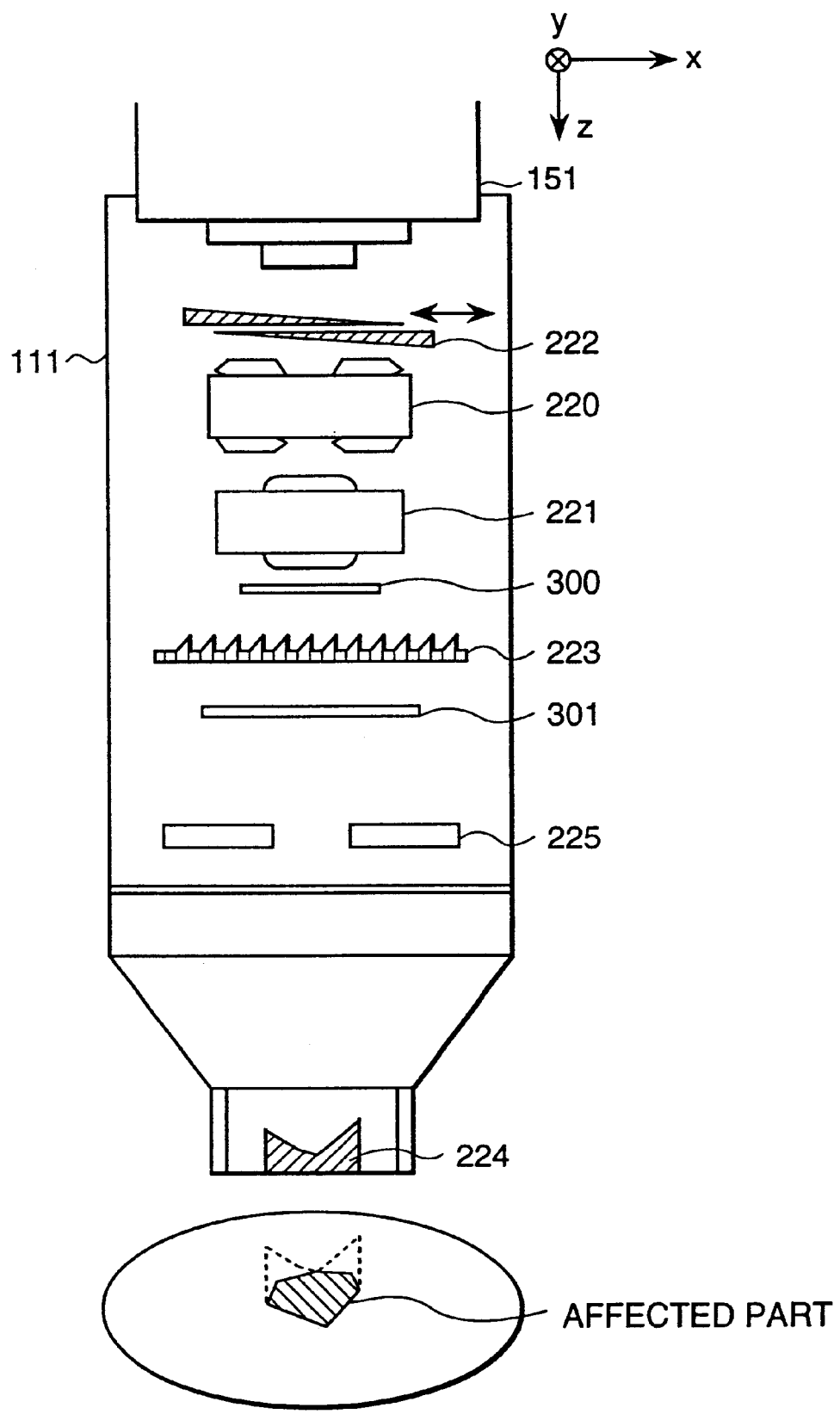
FIG. 6 is a schematic diagram of the irradiation nozzle 111 used in the first embodiment.

An example of the relationship between depth in a body and the irradiation dose of the ion beam is indicated in FIG. 5. The peak of the irradiation dose in FIG. 5 is called the Bragg peak. The position of the Bragg peak varies depending on the beam energy. Therefore, a range shifter 222 and a ridge filter 223 for adjusting the energy and the energy width of the beam, and a patient bolus 224 for changing the energy depending on the depth, direction, and shape of the affected part, are provided, as shown in FIG. 6. The ridge filter 223 has a saw tooth shape in the x direction, as shown in FIG. 6. The particle which passes through the peak portion of a saw tooth is reduced in energy to a large extent, and the particle which passes only through the bottom or base portion of a saw tooth is reduced in energy to a lesser extent. Therefore, an energy distribution based on the height of the peak portion and the depth of the bottom or base portion can be given to the beam. In accordance with the present invention, a ridge filter is used which causes the energy width of the charged particle beam coincide with a position where the affected part is deepest.

The operation unit 131 is a unit for determining data necessary for the control unit 132 to control the irradiation of the charged particle beam on-the affected part of the patient. The control unit 132 is an unit for controlling the extraction of the charged particle beam from the pre-accelerator 98 into the accelerator 100, for controlling the acceleration of the charged particle beam circulating through the accelerator 100, for controlling the extraction of the charged particle beam from the accelerator 100 into the rotational gantry 110, and for controlling the transport of the charged particle beam in the rotational gantry 110. The role of the operation unit 131 will first be described and a method for operating the charged particle beam apparatus by means of the control unit 132 will then be described.

Affected part information, such as the shape and the depth of the affected part, the required irradiation dose R, and information on the scatterer 300, such as thickness, materials, and so on, is input to the operation unit 131 by an operator. On the basis of the input of the affected part information and the scatterer information, the operation unit 131 calculates and determines the size of the beam, the irradiation region, the energy of the charged particle beam to be irradiated on the affected part, and the magnitude of current to be supplied to the electromagnets 220 and 221.

Figure 7:
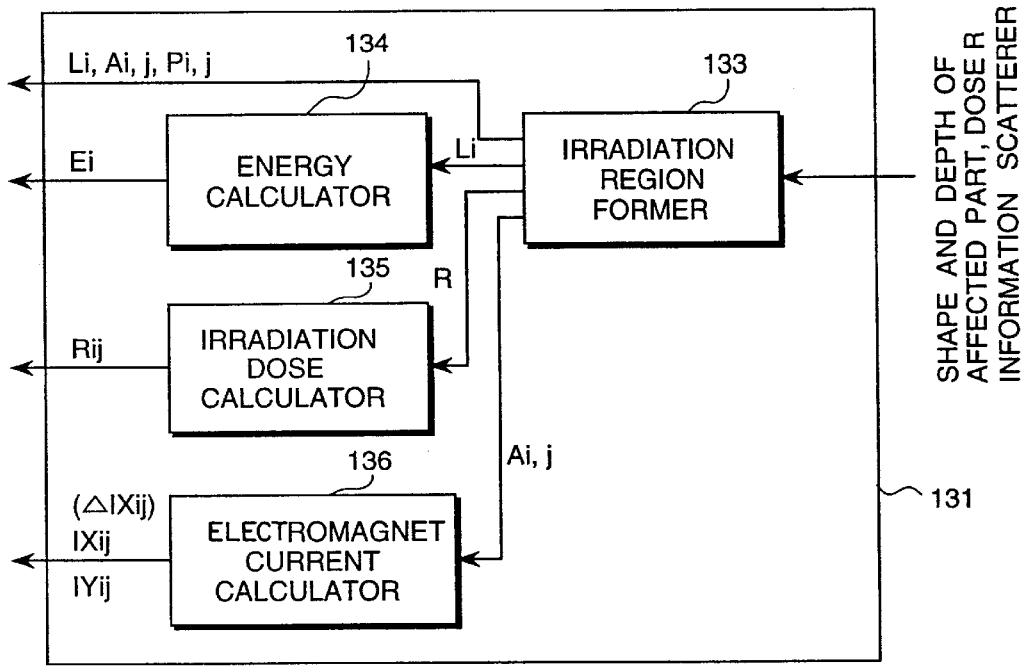
FIG. 7 is a block diagram of the operating unit 131 used in the first embodiment.
Figure 8:
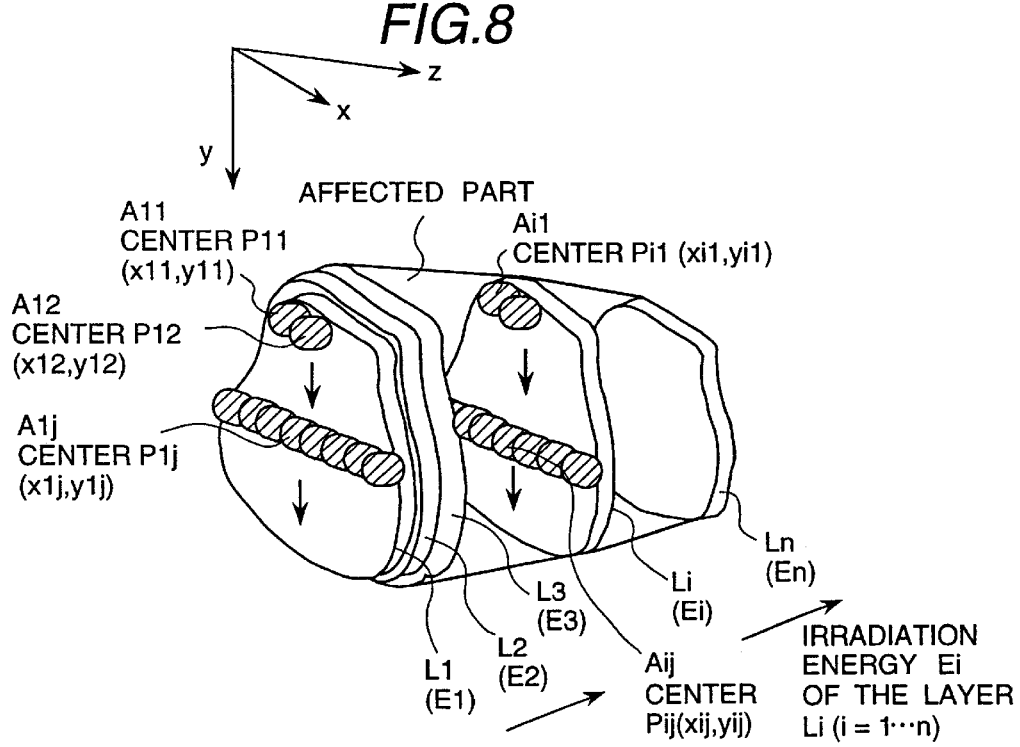
FIG. 8 is a perspective view of layers and irradiation regions of an affected part showing the method of irradiation used in the first embodiment.

An example of the operation unit 131 is shown in FIG. 7. An irradiation region former 133 of the operation unit 131 divides the effected part into a plurality of layers, as generally designated by Li (i=1, 2, ... N), in the depth direction on the basis of received affected part information, as shown in FIG. 8. An energy calculator 134 determines beam energy levels, as generally designated by Ei, suitable for irradiation in accordance with depths of the individual layers. Further, the irradiation region former 133 determines a plurality of irradiation regions as generally designated by Ai, j (i=1,2, ... N, j=1,2, ... N), center points Pi, j of the irradiation regions Ai, j, and coordinate values (xij, yij) of the center points in accordance with shapes of the individual layers Li.

Since the intensity of the charged particle beam is spatially distributed pursuant to a Gaussian distribution the operation unit 131 determines the individual irradiation regions Ai, j and their center points Pi, j on the basis of the size of the charged particle beam so as to form irradiation regions wherein the irradiation doses are made uniform by overlapping the irradiation region Ai, j with adjacent irradiation regions. Each of the center points Pi, j is separated from an adjacent center point by approximately a half of the size of the beam.

An irradiation dose calculator 135 determines target values of the irradiation dose at the individual center points Pi, j on the basis of the necessary irradiation close Ri, j. An electromagnet current calculator 136 determines the current IXij and IYij to be supplied to the electromagnets 220 and 221 in order that the center of the charged particle beam matches the individual center points Pi, j. The operation unit 131 delivers to the control unit 130 beam energy Ei, individual irradiation regions Ai, j, center points Pi, j, coordinate values (xij, yij) of the center points Pi, j, target values of the irradiation dose Ri, j, and current values IXij and IYij, which are determined in respect of the individual layers Li.

Figure 9:
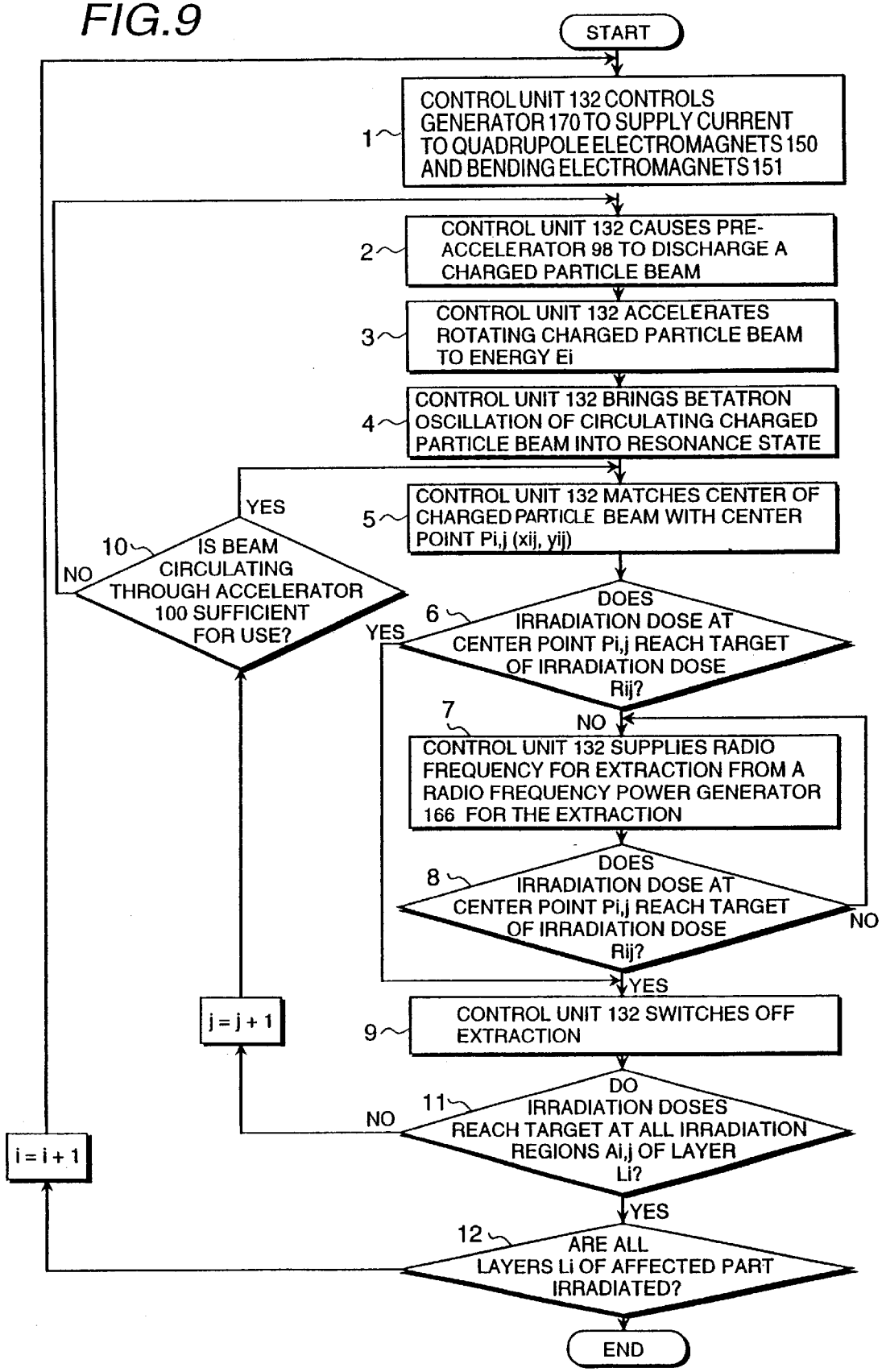
FIG. 9 is a flow chart showing a method for operating the medical charged particle beam apparatus of FIG. 3.

A method of operating the charged particle beam apparatus of FIG. 3 is shown in FIG. 9.

(1) The control unit 132 controls the power generator 170 to cause it to supply current to the quadrupole electromagnets 150 and the bending electromagnets 151 in order that a charged particle beam extracted from the accelerator 100 into the rotational gantry 110 will be transported to an affected part representing the irradiation target.

(2) The accelerator control unit 132 controls the pre-accelerator 98 to cause it to eject a charged particle beam.

(3) The control unit 132 controls the power generator 165 to supply current to the bending electromagnets 146, quadrupole electromagnets 145, and the multipole electromagnets 11, in order to accelerate the circulating charged particle beam to the energy level Ei, and controls the power generator 165 to supply electric power to the radio frequency accelerating cavity 147.

(4) When the circulating charged particle beam is accelerated to the energy level Ei, the control unit 132 controls the power generator 165 to cause it to supply current to the quadrupole electromagnets 145 and the multipole electromagnets 11 in order to generate the stability limit of the resonance of betatron oscillation. When electric power is supplied to the radio frequency applying unit for extraction 120, the betatron oscillation amplitude of the circulating charged particle beam increases, and this results in the resonance state of the betatron oscillation for the charged particle beam outside the stability limit.

(5) The control unit 132 controls the power generator 160 to cause it to supply current IXij and IYij to the electromagnets 220 and 221 in order that the center of the charged particle beam matches an optional center point Pi,i.

(6) The control unit 132 compares a target value of the irradiation dose Ri, j with an irradiation dose applied at the particular center point Pi, j measured by the irradiation dose monitor 301.

(7) When the irradiation dose applied at the particular center point Pi, j does not equal the target value of the irradiation dose Ri, j, the control unit 132 controls the radio frequency power generator for extraction 166 to cause it to supply electric power to the radio frequency applying unit for extraction 120 in order to start the extraction of the beam from the accelerator 100 to the rotational gantry 110.

When electric power is supplied to the radio frequency applying unit for extraction 120, a radio frequency electromagnetic field is applied to the circulating charged particle beam to increase the betatron oscillation amplitude of the circulating charged particle beam. When the betatron oscillation amplitude is increased until a stability limit of resonance of the betatron oscillation is exceeded, the charged particle beam is extracted from the accelerator 100 into the rotational gantry 110. In the rotational gantry 110, the charged particle beam is irradiated on the center point Pi, j optional irradiation region Ai, j.

(8) The control unit 132 compares the target value of the irradiation close Ri, j with an irradiation close et center point Pi, j measured by the irradiation dose monitor 301. When the irradiation dose at the center point Pi, j does not reach the target value of the irradiation dose Ri, j, the extraction is continued.

(9) When the irradiation close et the center point Pi, j reaches the target value of the irradiation dose Ri, j, the control unit 132 controls the radio frequency power generator for extraction 166 to cause it to switch off the extraction. Then, the irradiation control unit 130 controls the power generator 160 such that the center of the charged particle beam is shifted to a center point Pi, j+1 of the next irradiation region Ai, j+1.

(10) When the beam circulating through the accelerator 100 is sufficient for use at the time that irradiation on the irradiation region Ai, j shifts to irradiation on the irradiation region Ai, j+1, the operation is carried out starting with the step (4), but when the beam intensity and the extraction time are insufficient, the operation is carried out starting with the step (1) for the purpose of replenishing the charged particle beam.

(11) When the required irradiation doses have reached the target values at all irradiation regions Ai, j of an optional layer Li, the operation starting from the step (1) is carried out for the next layer Li+1, and all irradiation regions in the layer Li+1 are irradiated in a manner similar to that in the case of the layer Li.

(12) When irradiation on all of the layers Li of the affected part are completed, the operation of the charged particle beam apparatus ends.

In accordance with the above embodiment, the layers Li of the affected part can be irradiated with a uniform irradiation dose. Since the uneven irradiation region formed outside a boundary of the layer Li of the affected part is cut off by the collimator 225, an irradiation of the charged particle beam fitting the shape of the affected part can be performed. Since the cut off region is smaller in comparison with the cut off region of the conventional case, wherein circular scanning of the charged particle beam is performed, the therapy irradiation can be performed with a smaller beam loss. Although the irradiation position of the charged particle beam has been set by two electromagnets, the irradiation position can be set by providing the patient bed 112 with a movable structure and by controlling it using the control unit 132.

If the scatterer 300 is not used, the size of the irradiated charged particle beam is small. Therefore, intervals between respective irradiation positions must tee determined to tee extremely smell in order to obtain a uniform irradiation intensity distribution, and the therapy plan and the control of the irradiation become significantly more complex. In accordance with the present embodiments by using the scatterer 300, the charged particle beam has an approximately Gaussian distribution, and the size of the beam can be increased to an adequate area. Therefore, a uniform irradiation dose distribution can be realized without making the intervals between the respective irradiation positions extremely small.

As explained above, the charged particle beam apparatus of the present invention can form a uniform irradiation field, while reducing the loss of part of the charged particle beam. According to the present invention, even when the irradiation target has a complicated shape, the affected part can be irradiated with a high accuracy. Furthermore, since the irradiation is continued until the irradiation dose reaches a target value, the affected part can be irradiated with a uniform beam density even when the beam intensity changes with time.

Figure 10:
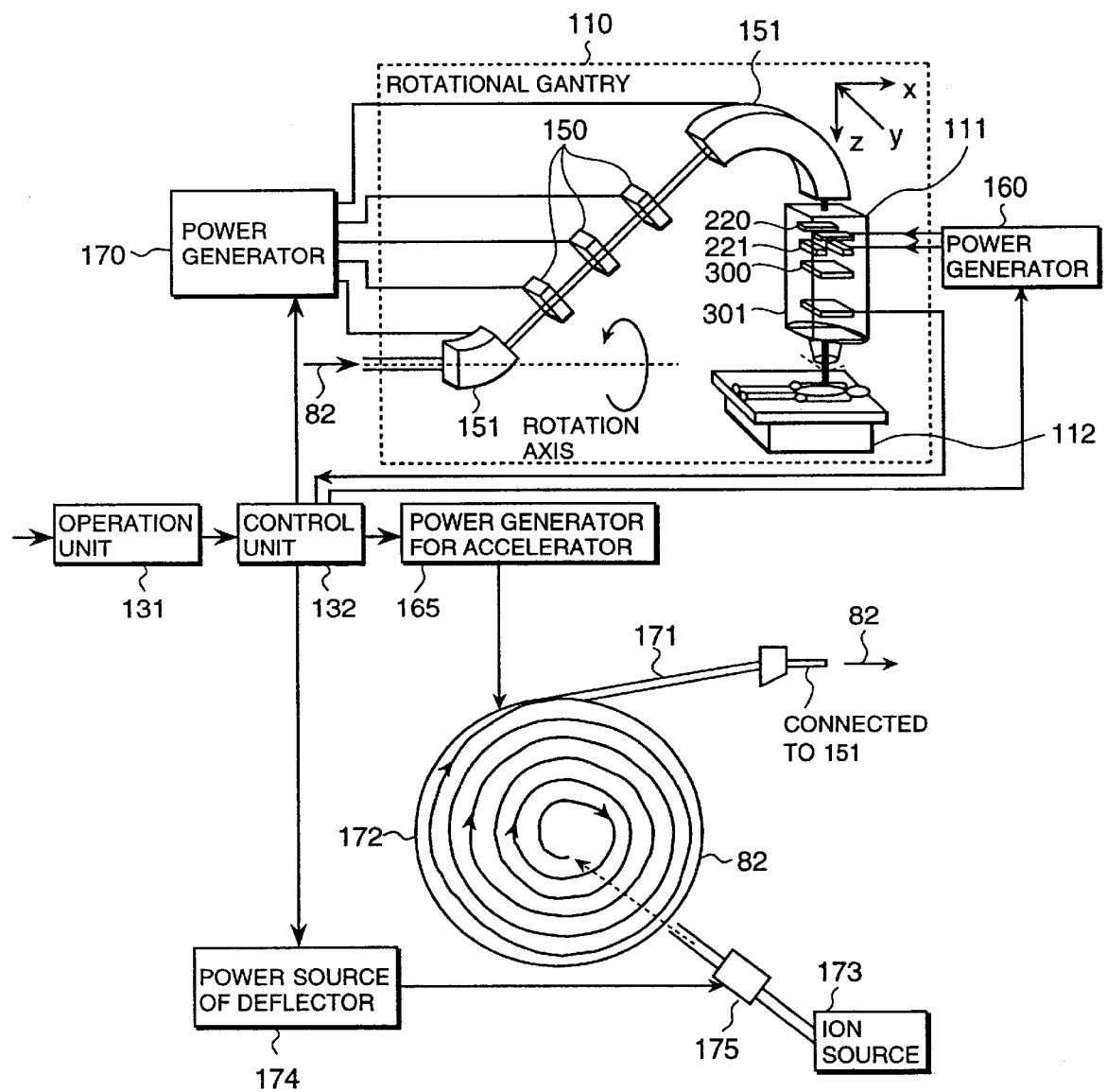
FIG. 10 is a schematic diagram showing a variation of the charged particle beam apparatus of FIG. 3, wherein a cyclotron is used rather than a synchrotron accelerator.

Although a synchrotron was used as the accelerator in the present embodiment, a cyclotron 172 can be used as the accelerator as shown in FIG. 10. The extraction and cutting off of the beam from the cyclotron 172 may be performed by controlling the power source 174 for the deflector 175 with signals from the control unit 132 or by controlling the supply of the charged particle beam from ion source 173.

Embodiment 2

Figure 11:
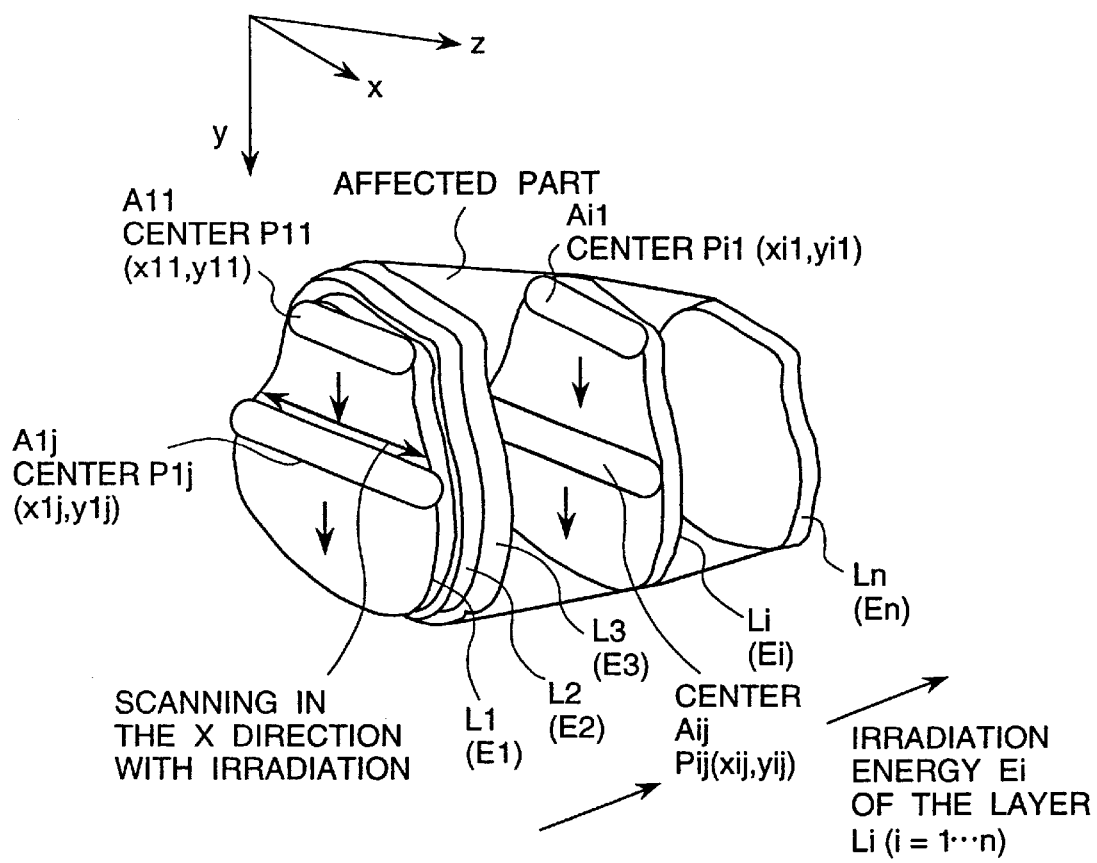
FIG. 11 is a perspective view of layers and irradiation regions of an affected part showing the method of irradiation used in a second embodiment of the present invention.

Next, a second embodiment of the present invention will be described. The construction of the charged particle beam apparatus of the present embodiment is similar to that of the first embodiment. In the present embodiment, however, each layer Li of an affected part is not divided in the x direction, but is divided only in the y direction, as shown in FIG. 11. In other words, the irradiation regions Ai, j are each elongated in the x direction. The elongated region Ai, j is irradiated by changing the strength of the magnetic field generated by the electromagnet 220 to scan the charged particle beam in the x direction.

The operation unit 131 determines a central point Pi, j of each of the irradiation regions Ai, j based on the size of the charged particle beam so as to form regions where a uniform irradiation dose is applied by overlapping the irradiation region Ai, j with adjacent irradiation regions in the y direction. The respective central points Pi, j are separated each from other by almost a half of the size of the beam.

The operation unit 131 determines the magnitude ΔXij necessary for changing the magnetic field strength of the electromagnet 220 on the basis of the extent of each region Ai, j in the x direction. As in the case of embodiment 1, the operation unit determines the beam energy Ei, individual irradiation regions Ai, j, their center points Pi, j (xij, yij), target values of the irradiation dose Rij, and current values IXij and IYij in respect of the individual layers Li, and delivers them, together with a value of the magnitude ΔIXij, to the control unit 132.

Figure 12:
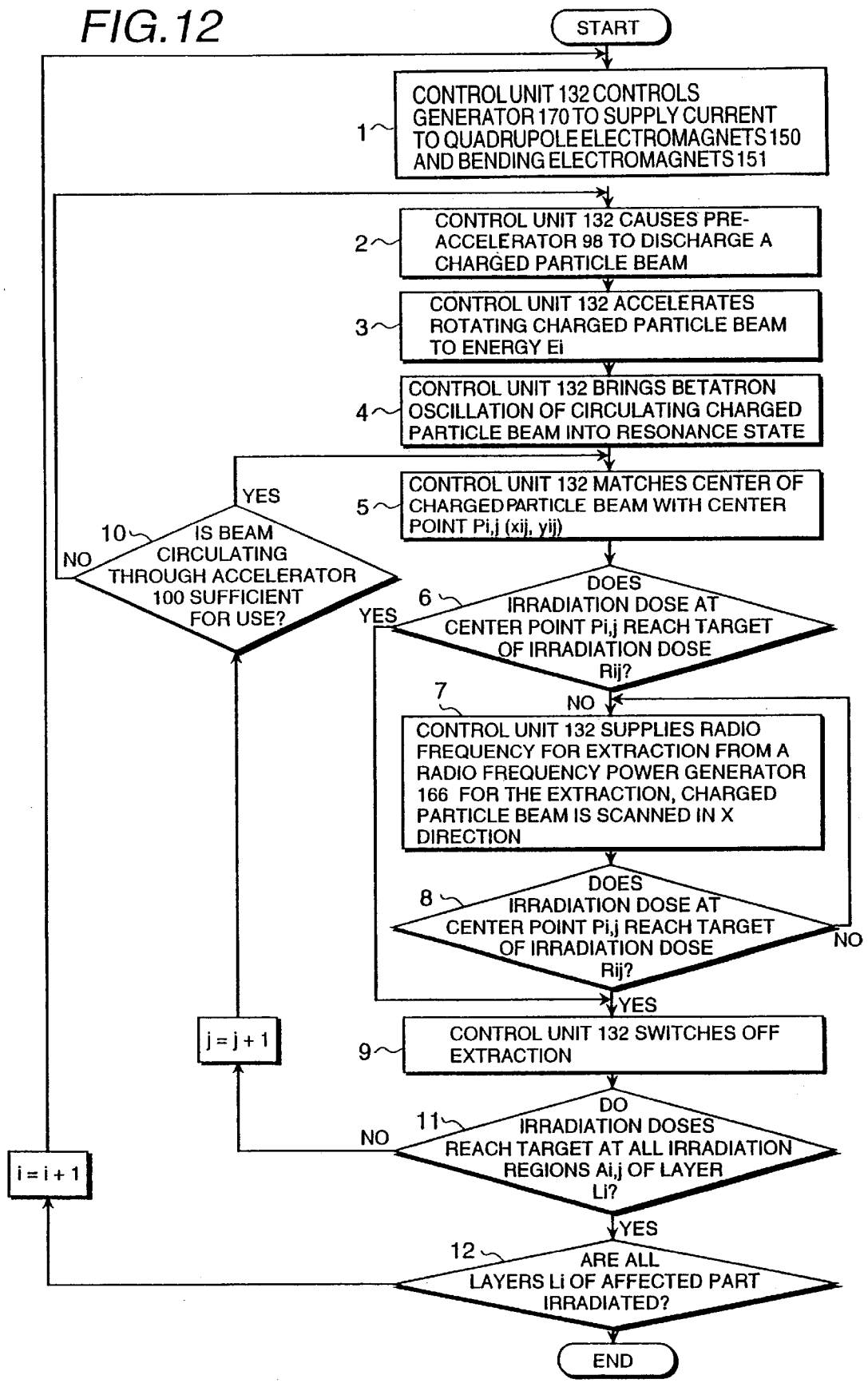
FIG. 12 is a flow chart showing the method for operating the medical charged particle beam apparatus in accordance with the second embodiment.

A method of operating the charged particle beam apparatus of the present invention according to this embodiment is shown in FIG. 12. Except for step (7), operation steps are the same as those of the first embodiment.

In the step (7), the control unit 132 controls the radio frequency power generator 166 to cause it to supply electric power to the radio frequency applying unit 120 in order that the extraction of the beam from the accelerator 100 into the rotational gantry 110 is started, and besides, the power generator 160 is controlled such that the current IXij to the electromagnet 220 changes within a range of ΔIXij to cause the charged particle beam to be irradiated while being scanned in the x direction.

While in the present embodiment, the strength of the magnetic field generated by the electromagnet 220 is changed to scan the charged particle beam in the x direction and irradiate it on the irradiation region Ai, j, the charged particle beam may be irradiated while being scanned in the y direction by changing the strength of the magnetic field generated by the electromagnet 221.

In accordance with the present embodiment, the same advantages as attained by the first embodiment can be obtained, and furthermore, the irradiation time can be shortened in comparison with the first embodiment, because switching between the extraction and stopping of the charged particle beam need be performed only when moving the beam in the y direction (or the x direction).

Embodiment 3

Figure 13:
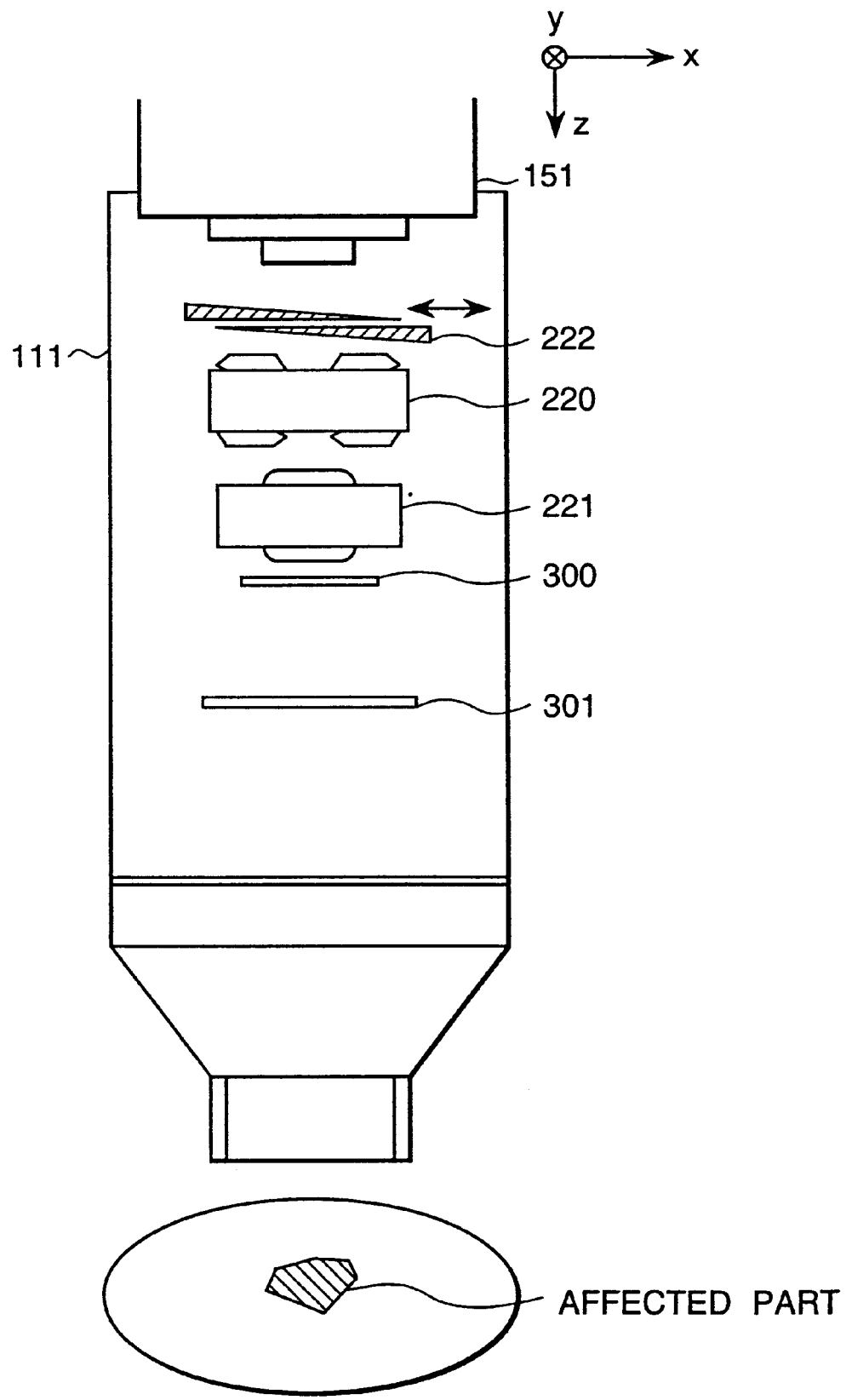
FIG. 13 is a schematic diagram of another form of the irradiation nozzle 111 which is used in a third embodiment of the invention.

Next, a third embodiment of the present invention will be explained. In accordance with the present embodiment, the charged particle beam apparatus generally has the same construction as the apparatus shown in FIG. 3, except for the composition of the irradiation nozzle 111 and the control unit 132. The irradiation nozzle 111 of the present embodiment is shown in FIG. 13.

In the present embodiment, the scatterer 300 is made thinner than that in the first embodiment. Since the size of the charged particle beam enlarged by the scatterer 300 becomes smaller than that in the first embodiment, the number of irradiation regions Ai, j is increased. On the other hand, since the size of the charged particle beam is small, the patient collimator, which has been used in the first embodiment, is not used in the present embodiment. Similarly, since the size of the beam becomes smaller than that in the first embodiment, the ridge filter and the bolus, which have been used in the first embodiment, are not used.

In accordance with the first embodiment, the energy of the charged particle beam is set to Ei by the accelerator 100. However, in accordance with the present embodiment, the energy of the charged particle beam is set to Ei by changing the thickness of the range shifter 222 during the time the extraction of the beam from the accelerator 100 is stopped by the control unit 132.

Figure 14:
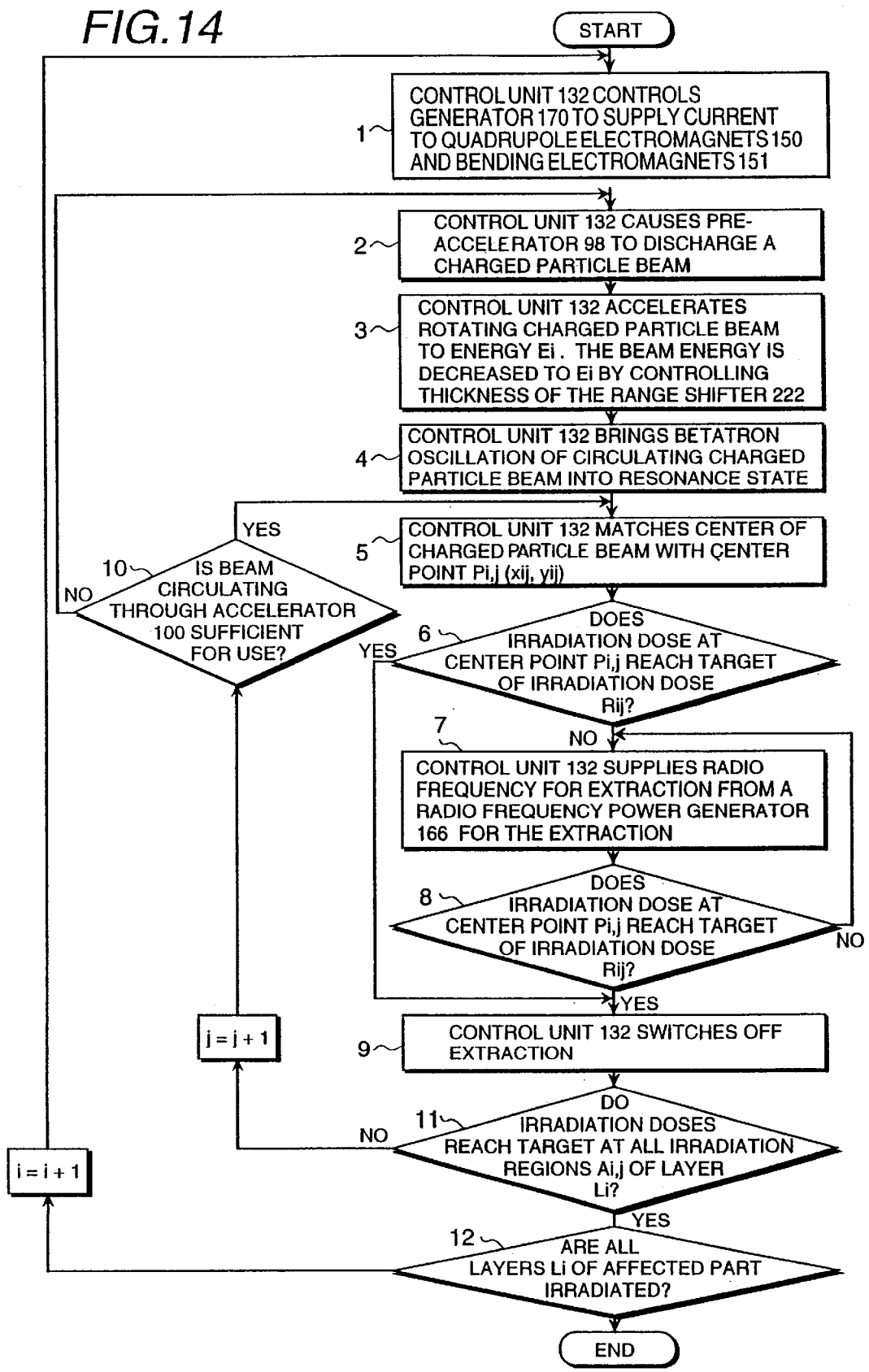
FIG. 14 is a flow chart showing another method for operating the medical charged particle beam apparatus of the present invention.

A method of operating the charged particle beam apparatus according to the present embodiment is shown in FIG. 14. The method is the same as that in the first embodiment, except for the steps (3) and (4).

In step (3), the control unit 132 controls the power generator 165 so as to supply current to the bending electromagnets 146 and quadrupole electromagnets 145, and to supply electric power to the radio frequency accelerating cavity 147 in order to accelerate the circulating charged particle beam to an energy level E, which is larger than the respective energy level Ei of the layers.

In step (4), when the circulating charged particle beam is accelerated to the energy level E, the control unit 132 controls the power generator 165 to cause it to supply currents to the quadrupole electromagnets 145 and the multipole electromagnets 11 in order to put the betatron oscillation of the circulating charged particle beam into a resonance state.

As described above, the charged particle beam apparatus according to the present embodiment can reduce the loss of part of the charged particle beam and can form a uniform irradiation field. The affected part can be irradiated precisely without using a collimator or a bolus per respective patient. In accordance with the present embodiment, the irradiation is performed by repeatedly changing of the intensity of the fields generated by the electromagnets 220,221 for setting the irradiation position, while setting a definite irradiation depth by controlling the thickness of the range shifter to a definite value. After irradiating a layer of a selected depth, the thickness of the range shifter is changed, and the irradiation is repeated using the same steps as described above.

However, the irradiation also can be performed by another method, wherein the target is divided supposedly into layers in parallel with the moving direction of the charged particle beam. In accordance with this method, the irradiation is performed under a condition of a definite intensity of the electromagnets 220, 221, then, the irradiation is stopped, the thickness of the range shifter is changed, and the irradiation is repeated. After irradiating all regions in a layer, the intensity of the electromagnets 220, 221 is changed to shift to the next layer, and the irradiation is repeated using the same steps as described above.

Embodiment 4

Figure 15:
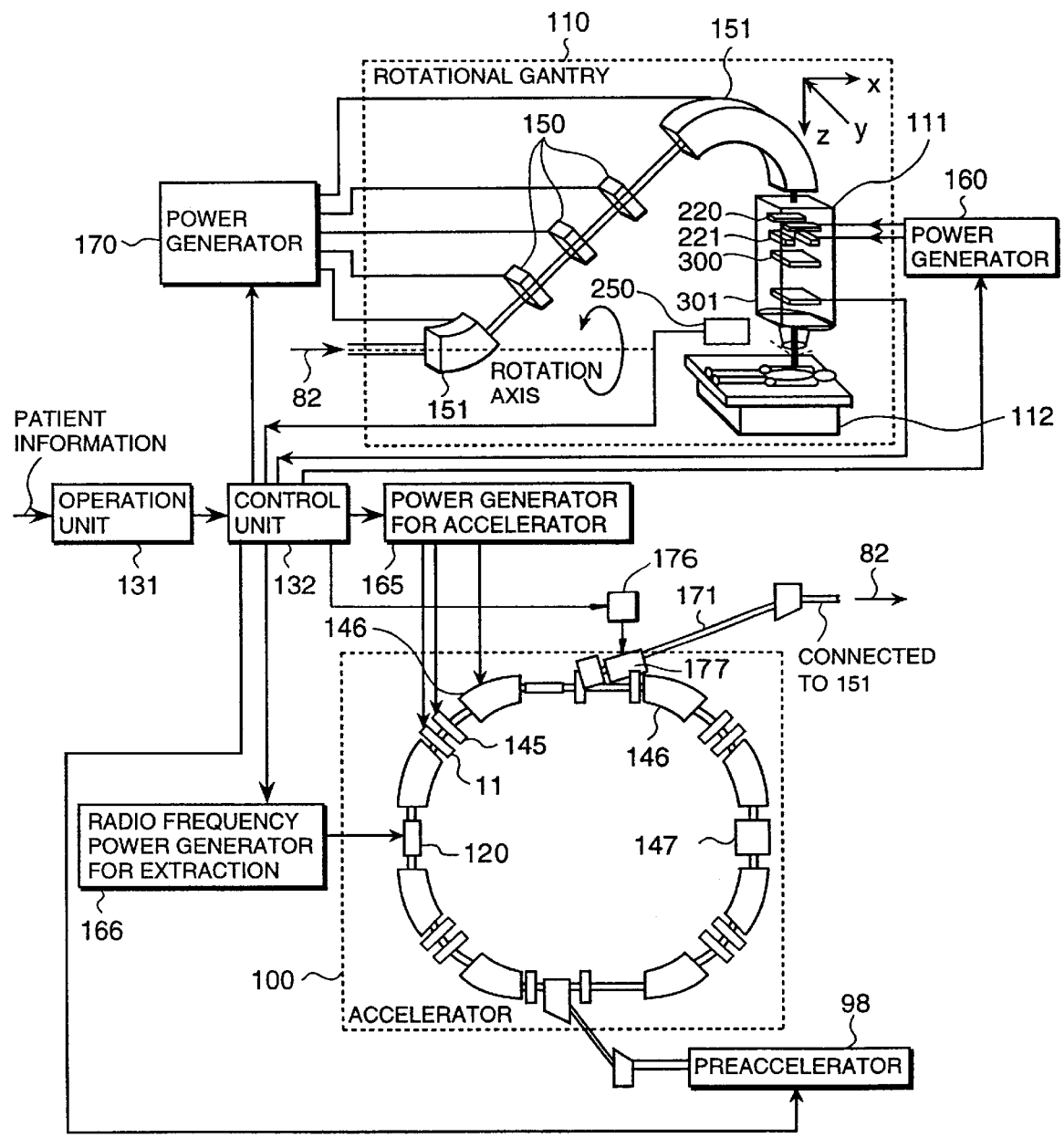
FIG. 15 is a schematic diagram showing a third embodiment of a charged particle beam apparatus of the present invention.

A fourth embodiment of the present invention will be explained hereinafter. An example of the construction of this embodiment is shown in FIG. 15. The difference from the embodiment 1 concerns the additional provision of a movement monitor 250 for detecting the movement of the patient's body, as well as an electromagnet 177 for switching between the supply and cut off of the charged particle beam and a power source 176 for the same as provided in the beam transport system 171 for transporting the charged particle beam to the irradiation apparatus. Other components in the apparatus are the same as in embodiment 1. The power source 176 is arranged so that the beam is not irradiated to the patient when electric current, does not flow due to failure of the power source, and the beam is irradiated to the patient only when electric current is supplied normally.

Figure 16:
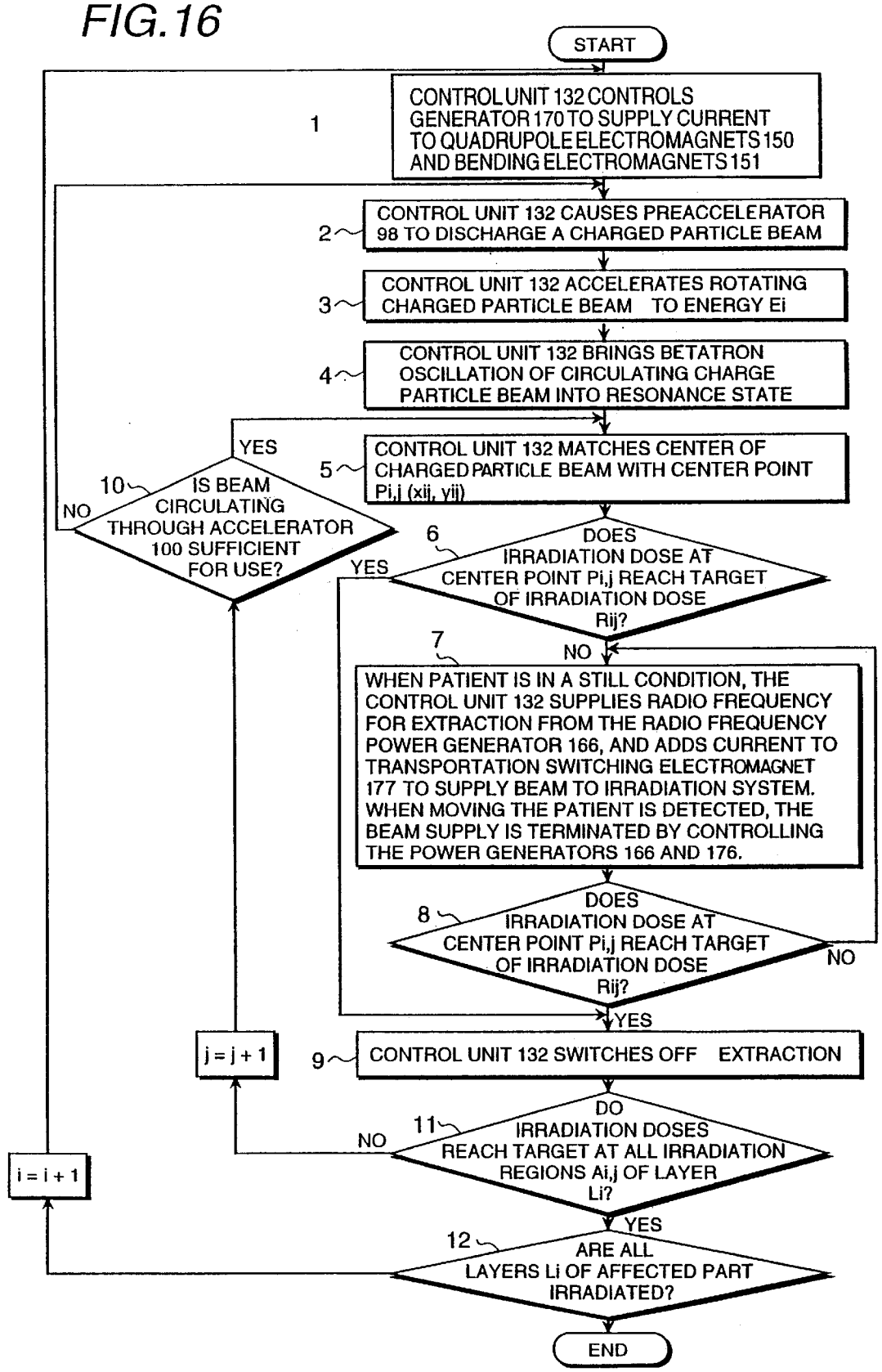
FIG. 16 is a flow chart showing the method for operating the medical charged particle beam apparatus of the third embodiment.

The movement monitor 250 can be a strain gauge provided at the surface of the patient's body, or a camera for defecting the movement of the patient. In accordance with a signal from the movement monitor 250, the movement of the patient's body is detected, and a signal to irradiate the beam to the patient's body is transmitted to the radio frequency power generator 166 and the power source 176 for the switching electromagnet 177 of the beam transport system only when there is no movement, i.e. when the patient's body is in a still condition. Only when the above signal is positive for the irradiation will the radio frequency power generator 166 provide a high frequency to the charged particle beam and the power source 176 supply electric current to the switching electromagnet 177 of the beam transport system, so that the charged particle beam can be supplied to the rotational gantry 110. The method of effecting such control according to the present embodiment is shown in FIG. 16. The operation steps of this method are the same as the method used in embodiment 1, except for the steps (7) and (9).

In the step (7), when the irradiation dose at the particular center point Pi, j has not reached the target of irradiation dose Ri, j, and the patient is determined to be in a still condition by the signal from the movement monitor 250, the control unit 132 controls the radio frequency power generator 166 to cause it to supply electric power to the radio frequency applying unit 120 in order to start the extraction from the accelerator 100 to the rotational gantry 110. Concurrently, electric current is supplied to the switching electromagnet 177 in the charged particle beam transport system from the power source 176. However, if it is determined that the patient is not in a still condition, the radio frequency power generator 166 and the power source 176 for the switching electromagnet 177 in the charged particle beam transport system are controlled so that the supply of the charged particle beam to the rotational gantry 110 is stopped.

In the step (9), when the irradiation dose at the particular center point Pi, j reaches the target value Ri, j, the control unit 132 controls the radio frequency power generator 166 to terminate the extraction of the charged particle beam and controls the power source 176 to stop supplying the electric current to the switching electromagnet 177 in the charged particle beam transport system in order to terminate supply of the charged particle beam to the rotational gantry 110. Then, the power source 160 is controlled so that the center of the charged particle beam is shifted to the center point Pi, j+1 of the next particular irradiation region Ai, j+1.

In accordance with the present embodiment, the same advantages as those attained by embodiment 1 can be obtained, and additionally, an advanced degree of safety can be obtained, because the switching of the irradiation is performed by two switching means. Furthermore, the irradiation target can be irradiated precisely, because the affected part can be irradiated with a charged particle beam when it is almost in a still condition.

Embodiment 5

Figure 17:
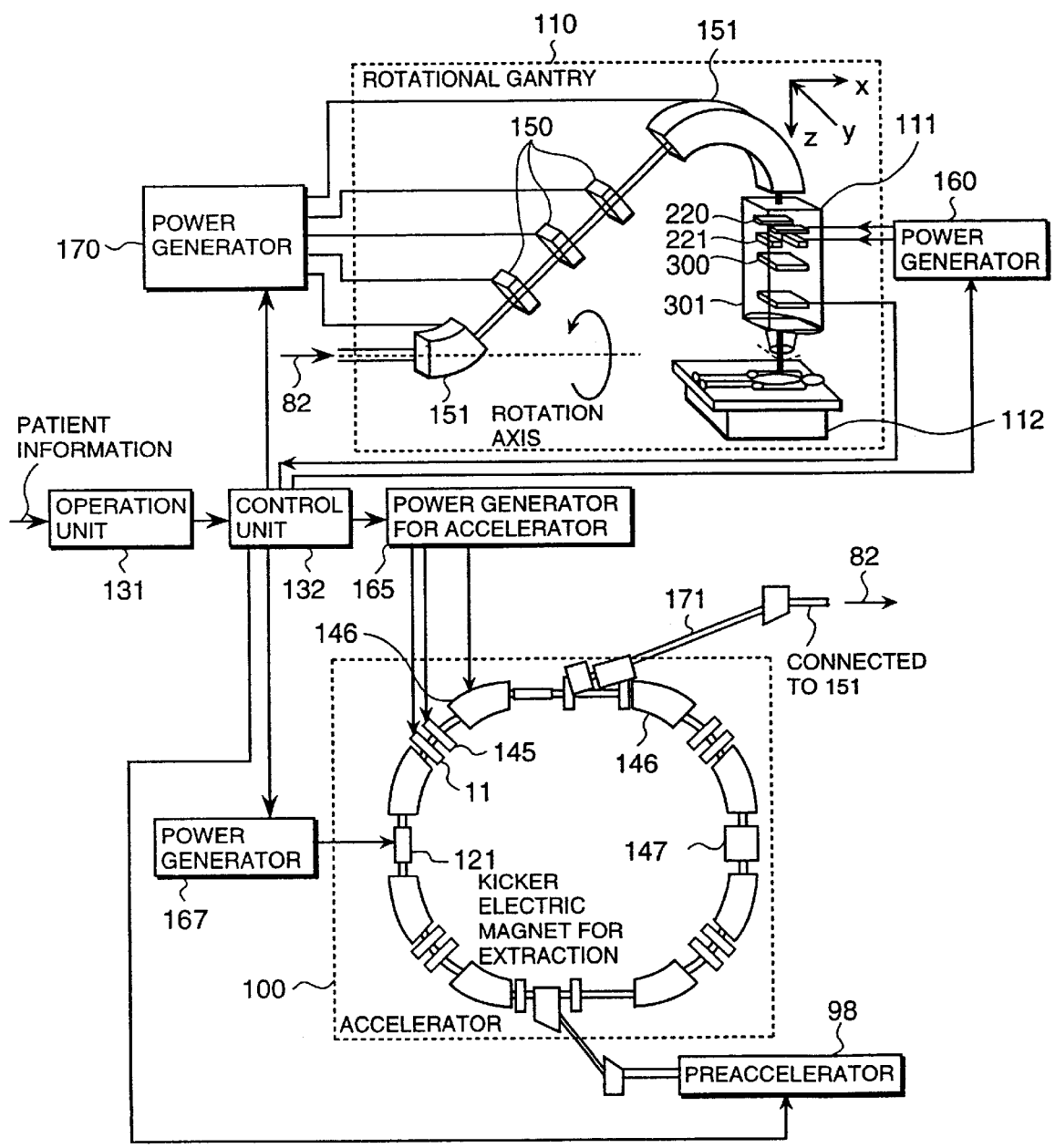
FIG. 17 is a schematic diagram showing a fourth embodiment of a charged particle beam apparatus of the present invention.

A fifth embodiment will be explained hereinafter. The composition of the apparatus according to the present embodiment is shown in FIG. 17. The main difference between the apparatus of this embodiment and that of the embodiment 1 is in the use of a kicker electromagnet for extraction 121 for extracting the beam from the accelerator in place of the radio frequency applying unit 120. The kicker electromagnet 121 extracts the circulating beam into the transport system 171 when it is pulse-excited with a power source 167 in response to signals from the control unit 132. Therefore, the beam is extracted as soon as the kicker electromagnet 121 is excited, and the beam extraction can be completed almost while the beam circulates only once in the accelerator. The division of the affected part is performed in the same manner as the embodiment 1, as shown in FIG. 8.

Figure 18:
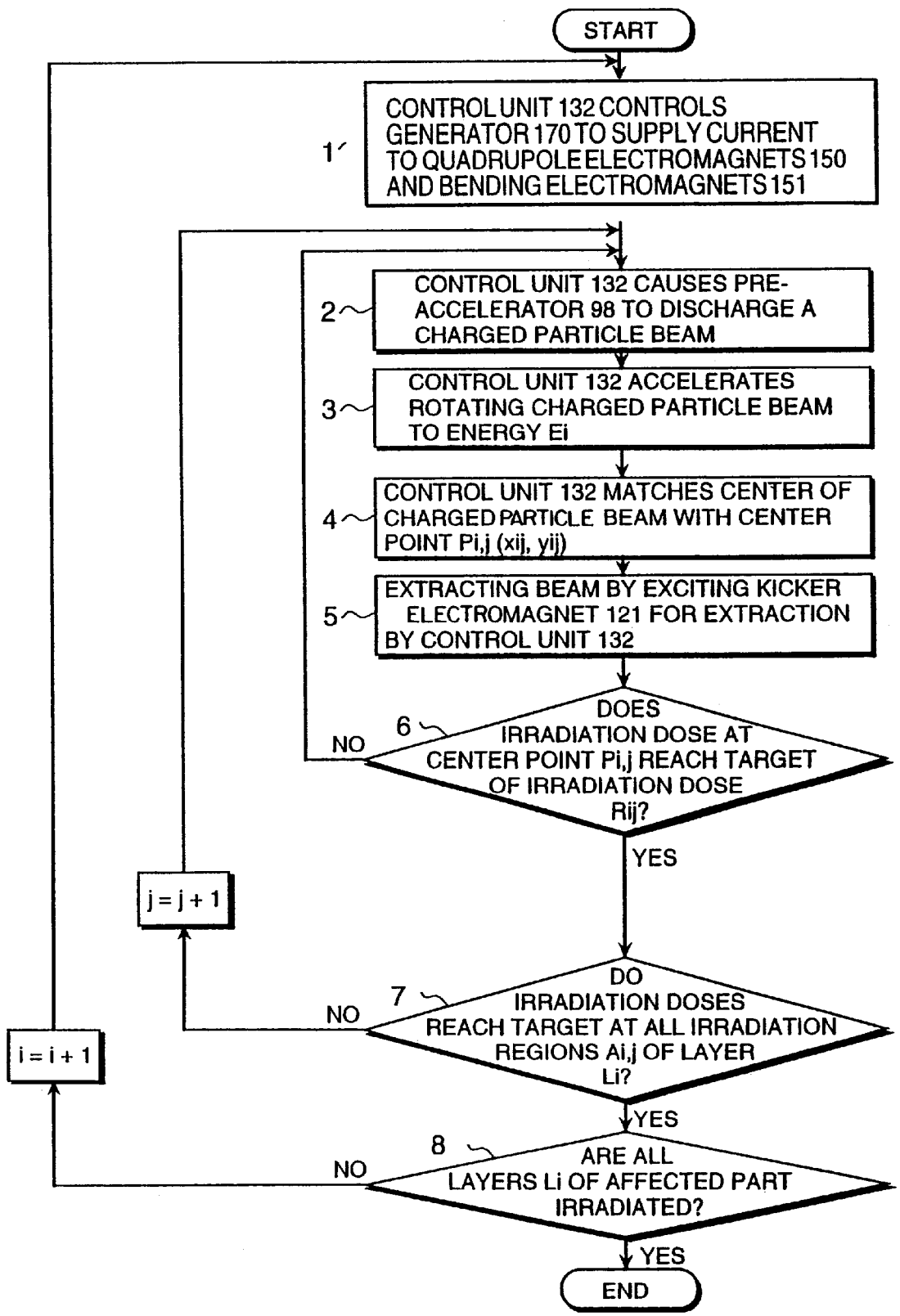
FIG. 18 is a flow chart showing a method for operating the medical charged particle beam apparatus of the fourth embodiment.

The method of operation of this embodiment is shown in FIG. 18. In the step (1), a magnitude of magnetic excitation of the electromagnet of the rotation gantry 110 is set so that a charged particle beam having the energy Ei can be transported in accordance with the signal from the control unit 132. Subsequently, the injection of the beam from the pre-accelerator 98 to the accelerator 100 and the acceleration and extraction of the beam are repeated in the steps (2) to (5). The beam is extracted as soon as the kicker electromagnet is excited, because the extraction is performed by the kicker electromagnet 121 in the present embodiment. Therefore, when the irradiation dose for respective partial regions Ai, j is judged to be insufficient in the step (6), the injection, acceleration, and extraction of the beam is repeated. Then, when the irradiation dose at the partial region Ai, j is judged to have reached the target value of the irradiation close in the step (6), the current values IXi, j, IYi, j of the electromagnets 220, 221 for setting the irradiation position are varied so as to shift the irradiation position in response to a signal from the control unit 132 in the step (4). When the irradiation of a layer Li is judged to be completed in the step (7), the injection, acceleration, and extraction of the beam are repeated for another irradiation layer until the irradiation of all of the layers is judged to have been completed in the step (8).

What is claimed is:

1. A method of irradiation with a charged particle beam, which is supplied from an accelerator to an irradiation apparatus comprising an electromagnet, and extracted from the irradiation apparatus for scanning with the charged particle beam, comprising the steps of:

stopping the extraction of the charged particle beam from the irradiation apparatus by stopping the supply of the charged particle beam from the accelerator to the irradiation apparatus;

changing an irradiation region of the charged particle beam by controlling the electromagnet under a condition when the extraction is stopped; and resuming the extraction of the charged particle beam from the irradiation apparatus after changing the irradiation region by resuming the supply of the charged particle beam from the accelerator;

wherein if the charged particle beam, which is circulating in the accelerator during the stopping of the extraction of the charged particle beam from the irradiation apparatus, is sufficient for irradiation at a new irradiation region after the changing of the irradiation region, a residual charged particle beam in the accelerator is supplied to the irradiation apparatus from the accelerator without supplying charged particles from a charged particle generator; and wherein if the residual charged particle beam in the accelerator is insufficient for irradiation at the new irradiation region after the changing of the irradiation region, supply of the residual charged particle beam in the accelerator to the irradiation apparatus from the accelerator is resumed after supplying of charged particles from the charged particle generator to the accelerator.

2. A method of irradiation with a charged particle beam as claimed in claim 1, wherein supplying of the charged particle beam from the accelerator to the irradiation apparatus is initiated by charging a high-frequency electromagnetic field to the charged particle beam which is circulating in said accelerator, and terminating the supplying of the charged particle beam from the accelerator to said irradiation apparatus by stopping the charging of the high-frequency electromagnetic field to the charged particle beam.

3. A method of irradiation with a charged particle beam as claimed in claim 1, wherein the step of changing the irradiation region is effected after an irradiation dose of the charged particle beam to the irradiation region has reached a pre-set value.

4. A method of irradiation with a charged particle beam as claimed in claim 1, wherein when irradiation of an affected part as the irradiation region is effected, the charged particle beam is extracted from the irradiation apparatus when the affected part is substantially stationary.

5. An accelerator system comprising:

an accelerator for supplying a charged particle beam;

an irradiation apparatus, which is provided with an electromagnet for scanning with the charged particle beam, for extracting the charged particle beam supplied from said accelerator; and a controller for stopping the extraction of the charged particle beam from the irradiation apparatus to an irradiation region by stopping supply of the charged particle beam from said accelerator, for changing the irradiation region of the charged particle beam by controlling the electromagnet under a condition when the extraction is stopped, and for resuming the extraction of the charged particle beam from the irradiation apparatus after changing the irradiation region by resuming the supply of the charged particle beam from the accelerator;

wherein the controller operates so that if the charged particle beam, which is circulating in the accelerator during the stopping the of extraction of the charged particle beam from the irradiation apparatus, is sufficient for irradiation at a new irradiation region after the changing of the irradiation region, the supply of the charged particle beam in the accelerator to the irradiation apparatus is resumed; and wherein if the charged particle beam, which is circulating in the accelerator during the stopping of the extraction of the charged particle beam from the irradiation apparatus is insufficient for irradiation at the new irradiation region after the changing of the irradiation region, the supply of the charged particle beam in the accelerator to the irradiation apparatus is resumed after supplying charged particles from a charged particle generator to the accelerator.

6. An accelerator system as claimed in claim 5, wherein the accelerator comprises a high-frequency charging apparatus for generating a high-frequency electromagnetic field, the controller operates so that the extraction of the charged particle beam from the irradiation apparatus is initiated by supplying the charged particle beam from the accelerator by generating a high-frequency electromagnetic field with the high-frequency charging apparatus, and the control enables termination of the extraction of the charged particle beam from the irradiation apparatus by stopping of the supply of the charged particle beam from the accelerator by stopping of the generation of the high-frequency electromagnetic field.

7. An accelerator system as claimed in claim 5, further comprising an irradiation dose monitor for measuring an irradiation dose of the charged particle beam at the irradiation region, and the controller operates so the changing of the irradiation region is effected after the irradiation dose of the charged particle beam to the irradiation region reaches a pre-set value.

* * * * *